United States Patent [19]

Rath et al.

[11] Patent Number: 4,708,802

[45] Date of Patent: Nov. 24, 1987

[54] APPARATUS FOR HEMODIAFILTRATION

[75] Inventors: Dieter Rath, Melsungen; Rolf Heitmeier, Baunatal, both of Fed. Rep. of Germany

[73] Assignee: Intermedicat GmbH, Emmenbrucke, Fed. Rep. of Germany

[21] Appl. No.: 897,704

[22] Filed: Aug. 18, 1986

[30] Foreign Application Priority Data

Aug. 22, 1985 [DE] Fed. Rep. of Germany ....... 3529973

[51] Int. Cl.$^4$ .............................................. B01D 13/00
[52] U.S. Cl. ................... 210/641; 210/651; 210/90; 210/433.2; 210/321.72
[58] Field of Search ............... 604/4, 5, 6; 210/433.2, 210/927, 195.2, 929, 321.3, 90, 87, 641, 651, 188

[56] References Cited

U.S. PATENT DOCUMENTS

| | | | |
|---|---|---|---|
| 3,795,318 | 3/1974 | Crane et al. | 210/929 X |
| 4,191,182 | 3/1980 | Popovich et al. | 604/6 |
| 4,486,303 | 12/1984 | Brous | 210/321.3 X |
| 4,582,598 | 4/1986 | Bilstad et al. | 210/927 X |
| 4,596,550 | 6/1986 | Troutner | 604/5 |

FOREIGN PATENT DOCUMENTS

WO82/03568 10/1982 PCT Int'l Appl. .

*Primary Examiner*—Frank Spear
*Attorney, Agent, or Firm*—Spensley Horn Jubas & Lubitz

[57] ABSTRACT

An apparatus for hemodiafiltration that maintains the blood concentration of the patient relatively constant. A pump is connected to a branch off the external flow path of the dialysator which pumps fluid to the circulation system of the patient to compensate for the patient's fluid loss through the hemodiafilter membrane. A suction pump which affects the transmembrane pressure across the hemodiafilter membrane is controlled to achieve the desired filtrate flow necessary to balance the return flow to the patient.

16 Claims, 1 Drawing Figure

4,708,802

APPARATUS FOR HEMODIAFILTRATION

BACKGROUND OF THE INVENTION

The present invention relates to an apparatus for hemodiafiltration, and more particularly to a hemodiafilter apparatus that continuously provides sufficient fluid to the blood circulation system of a patient to maintain the patient's blood concentration at a constant level.

Patients suffering from renal failure require artificial means for removing toxic substances accumulating in their bloodstream. Typically these patients undergo hemodialysis. In hemodialysis, blood of uremic patients is detoxified through a semipermeable membrane across which lies a concentration gradient. This concentration gradient causes certain particular toxic substances accumulated in the blood to diffuse from the bloodstream and into the dialysate. One disadvantage with hemodialysis is its inability to remove particles which are larger than the filter membrane typically used for dialysis. Another disadvantage with hemodialysis is the typically low flow rate of material transport across the dialysis membrane resulting from the concentration gradient.

One known dialysis means (U.S. Patent application No. 844,238) has attempted to deal with the disadvantage of low transmembrane dialysate flow by providing a pressure gradient across the dialysis filter. The pressure gradient is accomplished by placing upstream of the dialysis filter, a volume-controlled pump, and placing downstream of it, a suction pump responsive to the transmembrane pressure of the filter. The suction pump is controlled to keep the transmembrane pressure constant. As a result, the pressure gradient adds to the transmembrane dialysate flow rate caused by the concentration gradient. This dialysis means, however, is still limited by the filter membrane used for dialysis, which is impermeable to larger molecules. In addition, as a result of the increased flow rate, this dialysis means suffers the additional disadvantage of causing a thickening of the blood of the patient. As explained later, this problem is also exhibited in hemodiafiltration, another process used to avoid the conventional disadvantages of dialysis.

In hemodiafiltration, a hemodiafilter is used which allows the passage of molecules larger than those permitted by a dialysis filter. In addition, hemodiafiltration allows a much higher convective material transport through the membrane then conventional dialysis means. In addition, unlike dialysis, hemodiafiltration may be used to pass through the filter membrane components of the blood that do not show a difference in concentration across the filter membrane. Therefore, the number of components that may be removed from the blood in hemodiafiltration is considerably higher than that in hemodialysis. Consequently, hemodiafiltration suffers from a disadvantage in causing a thickening of the patient's blood by additional loss of blood fluid. As a result, it is necessary to replace the additional fluid lost by the patient.

In a known apparatus for hemodiafiltration that deals with the above fluid loss problem (German laid open patent application No. 32 13 390), blood is reinfused to the patient to offset any fluid loss. The amount of blood to be reinfused is determined by weighing the filtrate removed from the blood, and then administering to the patient the corresponding amount of substitution fluid. This method of weighing both the filtrate and the substitution solution suffers from the disadvantages of being tedious and time consuming. In addition, the patient suffers from a temporary condition of overly thickened blood.

It is the object of the present invention to provide a hemodiafiltration apparatus that reinfuses the patient with the required amount of substitution solution, in a continuous, quick, and easy manner, to avoid blood thickening of the patient.

SUMMARY OF THE INVENTION

This objective as well as others are achieved through the present invention by providing a hemodiafiltration apparatus whose external fluid path comprises a suction pump that is controllably responsive to the transmembrane filter pressure, and a volumetric pump connected to a separate branch off the external fluid path for pumping substitution solution to the patient's circulation system.

DESCRIPTION OF THE PREFERRED EMBODIMENT

Figure 1:
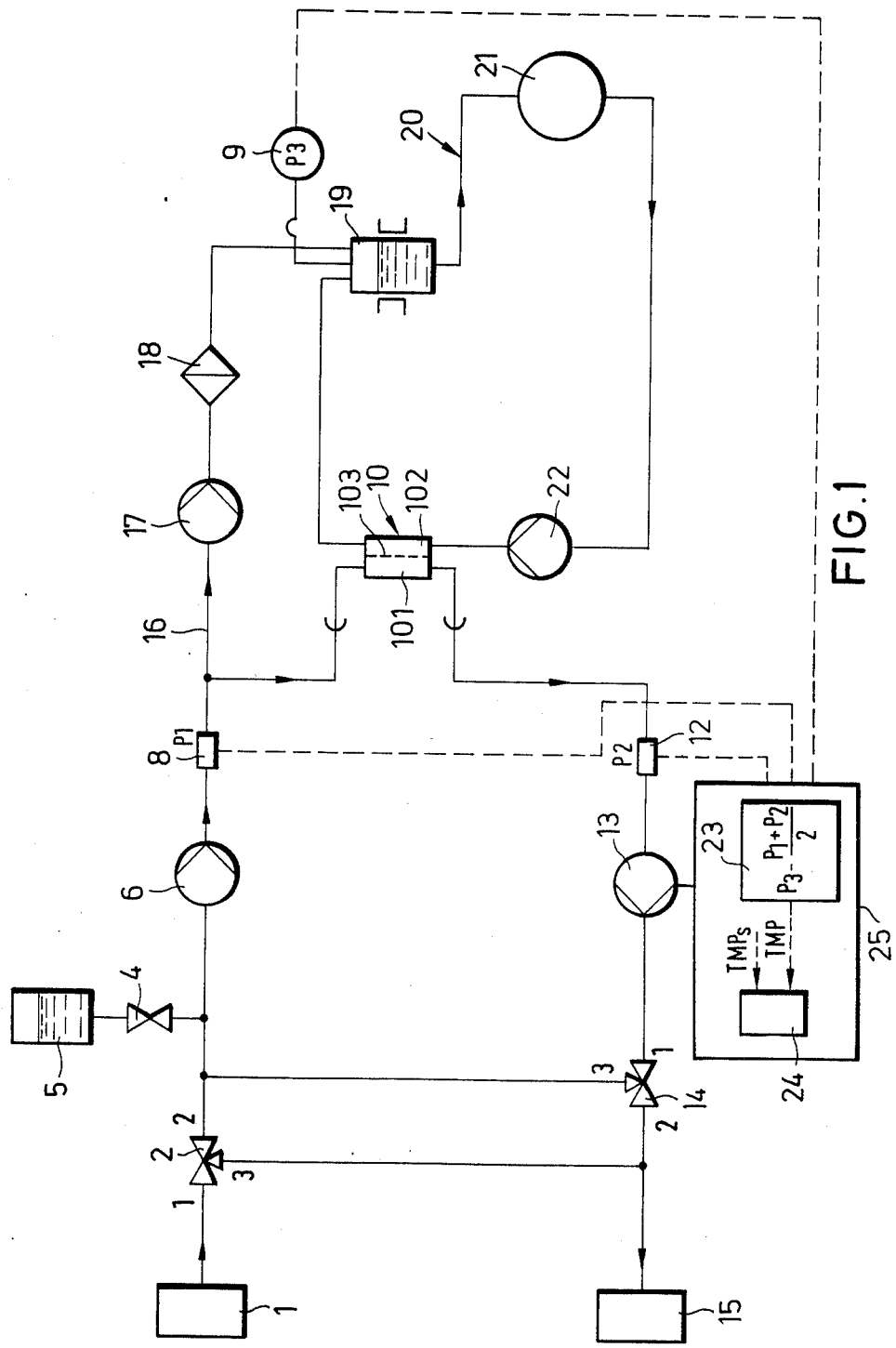
FIG. 1 is a flow diagram of a preferred embodiment of the present invention's hemodiafiltration apparatus as used with a patient.

The following detailed description is of the best presently contemplated mode of carrying out the invention. This description is not to be taken in a limiting sense, but is made merely for the purpose of illustrating the general principles of the invention. The scope of the invention is best defined by the appended claims.

Referring to FIG. 1, the following external fluid path is defined. A fluid source 1 is connected via a reversing valve 2 to a volumetric pump 6, which pumps fluid into a first volume chamber 101 of filter 10. A pressure meter 8, which interconnects pump 6 and chamber 101, measures pressure $P_1$. Suction pump 13, which is connected downstream of chamber 101, removes the accumulated fluid out of chamber 101. Pressure meter 12, which interconnects suction pump 13 and chamber 101, measures pressure $P_2$. Finally, the outlet side of suction pump 13 is connected to discharge 15 via reversing valve 14, thereby completing the external fluid path.

In addition to the external fluid path, there is defined a circulation fluid cycle 20, which includes the patient. In fluid path 20, the patient 21 is connected to a third pump 22, which maintains the blood flow of the patient while pumping blood into a second volume chamber 102 of filter 10. Blood entering chamber 102 is filtered across membrane 103 by the created pressure and concentration gradients across membrane 103. Any remaining fluid is pumped out of chamber 102 by pump 22 into buffer container 19, which returns fluid to the patient's circulatory system. Connected to buffer container 19 is pressure meter 9, which measures pressure $P_3$.

Fluid cycle 20 is of the closed type, i.e., buffer container 19 is completely sealed against outside air. Buffer container 19 contains a transparent wall and may be used as an air detector. If air is present in cycle 20, the fluid level in buffer container 19 drops. By varying the fluid level, the amount of air in cycle 20 may be controlled.

Connecting the external path and fluid cycle 20 is branch 16, a separate branch off the connection between volume-controlled pump 6 and chamber 101 of filter 10. Branch 16 includes a second pump 17, which is joined via a sterile filter 18 to buffer container 19.

The operation of the present invention will now be explained. In order to maintain the patient's blood concentration constant during hemodiafiltration, the transmembrane pressure across filter 10 is kept constant. This is achieved by controlling suction pump 13. With a constant transmembrane pressure, filter 10 passes a constant filtrate amount from the patient's fluid cycle 20 into the external fluid path. Since a constant fluid amount per unit time is removed from the patient, a second pump 17 may continuously compensate for the patient's fluid loss by regularly returning an equivalent amount of substitution solution to the patient. The substitution solution used derives from fluid source 1, the fluid of the external fluid path. Thus, by quantity control and without the need to weigh the transmembrane filtrate, the blood concentration of the patient is kept constant.

The method and apparatus for maintaining a constant transmembrane pressure will now be explained. The actual transmembrane pressure TMP of filter 10 is determined by the determination circuit 23 in accordance with the equation, $$TMP = P_3 - \frac{P_1 + P_2}{2}$$

In a comparator circuit 24, the value TMP is compared to a predetermined desired value $TMP_s$, the average transmembrane pressure necessary for the desired fluid flow across the filter. The difference between the two values, $TMP_s$ and TMP, is then used to control suction pump 13, either manually or automatically, through control means 25. By control means 25, the suction force developed by suction pump 13, which affects $P_2$, is maintained to always keep the transmembrane pressure TMP across filter 10 at or near the desired value $TMP_s$.

To determine $TMP_s$, the external fluid path is connected to a closed loop. This is achieved through valves 2 and 14, which connect the discharge path to the fluid source path. In addition, pumps 6 and 13 are temporarily stopped. Pump 17 is then operated at the approximate delivery rate required for the desired convective transport of matter across filter 10. The ensuing transmembrane pressure detected via sensors $P_1$, $P_2$ and $P_3$, is stored as a basic pressure in unit 24. In addition, a value corresponding to the filter's permeability may be calculated and stored as a filter parameter.

In addition to the above pressure and permeability parameters, the concentration gradient between the blood and fluid side need to be taken into account. In that case, it is necessary that the closed external fluid loop be opened by redirecting the discharge flow, through valves 2 and 14, back to discharge 15. In addition, pumps 6 and 13 are reactivated. Comparator circuit 24, through a preprogrammed algorithm, determines $TMP_s$ based on the concentration gradient and the above filter and basic pressure parameters. With $TMP_s$ set, the flow through filter membrane 103 during normal operation becomes the sum of the flow resulting from the pressure and concentration gradients. The amount of substitution solution administered to the patient through pump 17 is then adjusted to substantially correspond to the amount of fluid withdrawn through filter membrane 103.

As filter membrane 103 becomes more clogged with particulate matter, its ability to pass fluid will continually change. To maintain a balance of flow in and out of the patient during this entire transition period, it is imperative to periodically perform a redetermination of $TMP_s$. To this effect, valves 2 and 12 are switched into position to connect the dialysate source 1 to the discharge 15, thereby closing the external fluid cycle. In addition, pumps 6 and 13 are temporarily inactivated. Valve 4 is then opened so that a measuring container 5 is now opened to the external fluid path. Container 5 is connected to the external fluid path by a separate branch off the connection between valve 2 and pump 6.

Container 5 contains fluid identical to fluid source 1 and is preferably sealed from the outside air. The initial fluid level of container 5 corresponds to the equilibrium level of the fluid during the initial operation of the invention prior to any filter clogging. As a result, the fluid level in container 5 should rise or fall according to whether fluid is being added or removed from the closed cycle. Thus, if more fluid is being passed across the filter than is being returned to the patient, the fluid level should rise. Conversely, if more fluid is being added to the patient than is being passed across the filter, the fluid level should fall. Based on the rapidity of the fluid rise or fall in container 5, control means 25 is affected to control suction pump 13 in order to adjust $TMP_s$ to obtain a properly balanced filtrate flow.

The above description of the preferred embodiment is not to be seen as limiting. According to another embodiment of the invention, a third pump 22 may be in the cycle between the patient and the filter for maintaining the blood flow in the circulation system of the patient.

In addition, the present invention's apparatus for hemodiafiltration may be adapted for hemodialysis. In that case, the membrane of the filter needs to be replaced by a dialysis membrane suited to this effect. Moreover, either branch 16 should be blocked off or pump 17 should be disconnected.

What is claimed is:

1. An apparatus for hemodiafiltration of a patient, comprising:
   a fluid source,
   a first volumetric pump connected to said fluid source for pumping fluid out of said source,
   a hemodiafilter containing a filter membrane disposed between a first chamber and a second chamber, one end of said first chamber being connected by a first conduit to said first volumetric pump for receiving said pumped fluid, one end of said second chamber being connected by a second conduit to the patient,
   a suction pump connected to the other end of said first chamber for removing fluid out of said first chamber, said suction pump being operable to maintain a constant transmembrane pressure across the filter membrane, and
   a second volumetric pump connected between said first conduit and said second conduit, said second volumetric pump being operable to deliver fluid from said first conduit to said second conduit,
   whereby fluid lost from the second chamber during hemodiafiltration is replaced in substantially equal quantity by fluid delivered from said first conduit to said second conduit by said second volumetric pump.

2. An apparatus according to claim 1, further comprising a filter connected to said second volumetric pump for filtering the fluid delivered by said second volumetric pump.

3. An apparatus according to claim 1, further comprising air regulation means for regulating air quantity entering into said patient's circulatory system, said air regulation means being interconnected between said second volumetric pump and said patient's circulatory system.

4. An apparatus according to claim 1, further comprising measuring means for measuring a change in flow across said hemodiafilter, said measuring means being connected through a valve to said connection between said fluid source and said first volumetric pump.

5. An apparatus according to claim 4, wherein the outlet side of said suction pump is connected to the outlet side of said fluid source upstream of said measuring means via one or more valves, said one or more valves controllably diverting the outlet fluid flow from said suction pump to said fluid source.

6. An apparatus according to claim 1, further comprising:
a first pressure meter interconnected between said first volumetric pump and said first chamber for measuring fluid pressure between said first volumetric pump and said first chamber,
a second pressure meter interconnected between said suction pump and said first chamber for measuring fluid pressure between said suction pump and said first chamber, and
a third pressure meter interconnected between said second chamber and said patient for measuring fluid pressure between said patient and said second chamber.

7. An apparatus according to claim 6, further comprising:
control means operative on said suction pump for controlling pressure across said hemodiafilter, said control means including
means for determining an actual transmembrane pressure of said hemodiafilter, and
comparison means for comparing said actual transmembrane pressure to a predetermined desired value of a transmembrane pressure.

8. An apparatus according to claim 7, wherein said determination means calculates said acutal transmembrane pressure according to an algorithm, $$P_3 - \frac{P_1 + P_2}{2}$$

where $P_1$ is the fluid pressure measured by said first pressue meter, $P_2$ is the fluid pressure measured by said second pressure meter, and $P_3$ is the fluid pressure measured by said third fluid meter.

9. An apparatus according to claim 7 wherein said control means is automatic.

10. An apparatus according to claim 1, further comprising a third pump interconnected between said second chamber and said patient for delivering blood from said patient to said second chamber.

11. An apparatus for hemodiafiltration of a patient's blood comprising:
a hemodiafilter having a filter membrane disposed between a first chamber and a second chamber,
a first fluid conduit in communication with the first chamber,
a first pump for delivering fluid through said first fluid conduit to said first chamber,
a second pump in communication with said first chamber for removing fluid from said first chamber, said second pump being operable to maintain a constant pressure across the filter membrane of the hemodiafilter,
a second fluid conduit in communication with the second chamber and in communication with the patient,
a third fluid conduit in communication with the first fluid conduit at a location between the first pump and the first chamber and in communication with the second fluid conduit at a location between the second chamber and the patient,
a third pump for delivering fluid through the third fluid conduit from the first fluid conduit to the second fluid conduit,
whereby fluid lost from the second chamber during hemodiafiltration is replaced in substantially equal quantity by fluid delivered from the first fluid conduit to the second fluid conduit through the third fluid conduit.

12. An apparatus as in claim 11 further comprising:
a sterile filter for filtering the fluid delivered through the third conduit.

13. An apparatus as in claim 11 further comprising:
a buffer container in communication with the second conduit and the third conduit, the buffer container including an air detector for detecting air in the second conduit.

14. An apparatus as in claim 11 further comprising:
monitoring means for monitoring the ultrafiltration rate of the hemodiafilter.

15. An apparatus as in claim 11 wherein said first pump and said second pump are volumetric pumps.

16. In a hemodiafiltration system of the type wherein blood from a patient is filtered through a hemodiafilter having a filter membrane disposed between a first chamber and a second chamber, a method of compensating for fluid loss from the second chamber during hemodiafiltration comprising the steps of:
directing fluid from a fluid source to the first chamber through a first conduit,
removing fluid from the first chamber at a rate such that the pressure across the filter membrane of the hemodiafilter remains constant,
directing fluid from the second chamber to the patient through a second conduit,
diverting fluid from the first conduit to the second conduit,
whereby fluid lost from the second chamber during hemodiafiltration is replaced in substantially equal quantity by fluid diverted from the first conduit to the second conduit.

* * * * *